United States Patent
Komatsu et al.

(10) Patent No.: US 9,403,158 B2
(45) Date of Patent: Aug. 2, 2016

(54) METHOD FOR PRODUCING ESTER COMPOUND AND PALLADIUM CATALYST USED IN THE METHOD

(71) Applicant: JX NIPPON OIL & ENERGY CORPORATION, Chiyoda-ku, Tokyo (JP)

(72) Inventors: Shinichi Komatsu, Tokyo (JP); Akira Shibashi, Tokyo (JP); Takaya Matsumoto, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 14/431,849

(22) PCT Filed: Sep. 24, 2013

(86) PCT No.: PCT/JP2013/075693
§ 371 (c)(1),
(2) Date: Mar. 27, 2015

(87) PCT Pub. No.: WO2014/050810
PCT Pub. Date: Apr. 3, 2014

(65) Prior Publication Data
US 2015/0343432 A1    Dec. 3, 2015

(30) Foreign Application Priority Data
Sep. 28, 2012 (JP) ................... 2012-217653

(51) Int. Cl.
*C07F 15/00* (2006.01)
*B01J 31/22* (2006.01)
*C07C 67/38* (2006.01)

(52) U.S. Cl.
CPC ............. *B01J 31/2239* (2013.01); *C07C 67/38* (2013.01); *B01J 2231/32* (2013.01); *B01J 2231/321* (2013.01); *B01J 2531/0219* (2013.01); *B01J 2531/824* (2013.01); *C07C 2102/42* (2013.01); *C07C 2103/94* (2013.01)

(58) Field of Classification Search
CPC .................................................. B01J 31/2239
USPC ........................................................... 556/136
See application file for complete search history.

(56) References Cited

U.S. PATENT DOCUMENTS

2013/0079490 A1* 3/2013 Matsumoto ........... C07C 69/757
528/128

FOREIGN PATENT DOCUMENTS

| JP | H07-138205 A | 5/1995 |
| JP | H07-179400 A | 7/1995 |
| WO | 2011/099518 A1 | 8/2011 |

OTHER PUBLICATIONS

Bachkmutov et al., DaltonTransactions, 2005(11), 1989-1992.*
International Search Report dated Dec. 17, 2013, issued in International Application PCT/JP2013/075693.
Vladimir I. Bakhmutov et al., "Non-trivial behavior of palladium (II) acetate", Dalton Transactions, 2005, vol. 11, pp. 1989-1992.
R.F. Mulagaleev et al., "Palladium (II) Acetates: Synthesis and Molecular Transformation Scheme", Russian Journal of Applied Chemistry, 2010, vol. 83, No. 12, pp. 2065-2075.
Office Action mailed Nov. 30, 2015, for Chinese patent Application No. 201380051116.1, together with English translation thereof.

* cited by examiner

*Primary Examiner* — Porfirio Nazario Gonzalez
*Assistant Examiner* — Kofi Adzamli
(74) *Attorney, Agent, or Firm* — Fitch, Even, Tabin & Flannery LLP

(57) ABSTRACT

A method for producing an ester compound includes reacting a compound having at least one cyclic structure of a norbornene ring and a norbornadiene ring with an alcohol and carbon monoxide by using a palladium catalyst and an oxidizing agent, to thereby introduce ester groups to carbon atoms forming a double bond in the cyclic structure and obtaining the ester compound, wherein the palladium catalyst includes a palladium acetate having a nitrite ligand in an amount of 10% by mole or more in terms of metal, and the palladium acetate having a nitrite ligand is represented by the general formula (1): $Pd_3(CH_3COO)_5(NO_2)$.

4 Claims, 8 Drawing Sheets

US 9,403,158 B2

METHOD FOR PRODUCING ESTER COMPOUND AND PALLADIUM CATALYST USED IN THE METHOD

CROSS-REFERENCE TO RELATED APPLICATIONS

This Application is a U.S. National Stage Application filed under 35 U.S.C. §371 of International Application PCT/JP2013/075693, filed Sep. 24, 2013, designating the United States, which claims priority from Japanese Patent Application 2012-217653, filed Sep. 28, 2012, the complete disclosures of which are hereby incorporated herein by reference in their entirety for all purposes.

TECHNICAL FIELD

The present invention relates to a method for producing an ester compound and a palladium catalyst used in the method.

BACKGROUND ART

Conventionally, as a method for obtaining an ester compound, a method (a method utilizing so-called the oxidative alkoxycarbonylation reaction (esterification reaction)) has been known in which a norbornene-based compound having a carbon-carbon double bond is reacted with an alcohol and carbon monoxide by using a palladium catalyst to thereby introduce (add) ester groups to the carbon atoms forming the double bond and obtain the ester compound. For example, International Publication No. WO2011/099518 (PTL 1) discloses a method for obtaining an ester compound in which a norbornene is reacted with an alcohol and carbon monoxide by using a palladium catalyst and an oxidizing agent to thereby introduce ester groups into the carbon atoms forming the carbon-carbon double bond (olefinic double bond) in the norbornene. In addition, PTL 1 mentioned above discloses palladium catalysts usable in the method for obtaining an ester compound, such as palladium chloride, palladium nitrate, palladium sulfate, palladium acetate, palladium propionate, palladium carbon, palladium alumina, and palladium black.

CITATION LIST

Patent Literature

[PTL 1] International Publication No. WO2011/099518

SUMMARY OF INVENTION

Technical Problem

However, when a norbornene is reacted with an alcohol and carbon monoxide by using any of the conventional palladium catalysts such as palladium chloride, palladium nitrate, palladium sulfate, palladium acetate, palladium propionate, palladium carbon, palladium alumina, and palladium black as disclosed in PTL 1, the formation of by-products cannot necessarily be suppressed sufficiently, and the ester compound cannot necessarily be produced with a sufficient selectivity.

The present invention has been made in view of the problem of the above-described conventional technology, and an object of the present invention is to provide a method for producing an ester compound by which the formation of by-products can be sufficiently suppressed, and the ester compound can be produced efficiently with a sufficiently high selectivity, as well as a palladium catalyst used in the method.

Solution to Problem

The present inventors have conducted intensive study to achieve the above-described object, and consequently found that, in a method for producing an ester compound, comprising reacting a compound having at least one cyclic structure of a norbornene ring and a norbornadiene ring with an alcohol and carbon monoxide by using a palladium catalyst and an oxidizing agent, to thereby introduce ester groups (alkoxycarbonyl groups) to the carbon atoms forming a double bond in the cyclic structure and obtain the ester compound, the use of a palladium catalyst comprising a palladium acetate having a nitrite ligand and being represented by the following general formula (1) in an amount of 10% by mole or more in terms of metal as the palladium catalyst makes it possible to sufficiently suppress the formation of by-products (polymerization products formed by addition polymerization of the cyclic structure (the portion of the structure of the norbornene ring and/or the norbornadiene ring), reaction intermediates, and the like), and to efficiently produce the ester compound with a sufficiently high selectivity. This finding has led to the completion of the present invention.

Specifically, a method for producing an ester compound of the present invention is a method for producing an ester compound comprising reacting a compound having at least one cyclic structure of a norbornene ring and a norbornadiene ring with an alcohol and carbon monoxide by using a palladium catalyst and an oxidizing agent, to thereby introduce ester groups to carbon atoms forming a double bond in the cyclic structure and obtain the ester compound, wherein the palladium catalyst comprises a palladium acetate having a nitrite ligand in an amount of 10% by mole or more in terms of metal, and the palladium acetate having a nitrite ligand is represented by the following general formula (1):

$$Pd_3(CH_3COO)_5(NO_2) \qquad (1).$$

The palladium catalyst according to the present invention preferably comprises the palladium acetate having a nitrite ligand in an amount of 30% by mole or more in terms of metal.

Meanwhile, a palladium catalyst of the present invention is a palladium catalyst used with an oxidizing agent in a method for producing an ester compound, the method comprising reacting a compound having at least one cyclic structure of a norbornene ring and a norbornadiene ring with an alcohol and carbon monoxide, to thereby introduce ester groups to carbon atoms forming a double bond in the cyclic structure and obtain the ester compound, wherein the palladium catalyst comprises a palladium acetate having a nitrite ligand in an amount of 10% by mole or more in terms of metal, and the palladium acetate having a nitrite ligand is represented by the following general formula (1):

$$Pd_3(CH_3COO)_5(NO_2) \qquad (1).$$

Moreover, the palladium catalyst of the present invention preferably comprises the palladium acetate having a nitrite ligand in an amount of 30% by mole or more in terms of metal.

Advantageous Effects of Invention

According to the present invention, it is possible to provide a method for producing an ester compound by which the formation of by-products can be sufficiently suppressed, and the ester compound can be produced efficiently with a sufficiently high selectivity, as well as a palladium catalyst used in the method.

DESCRIPTION OF EMBODIMENTS

Figure 1:
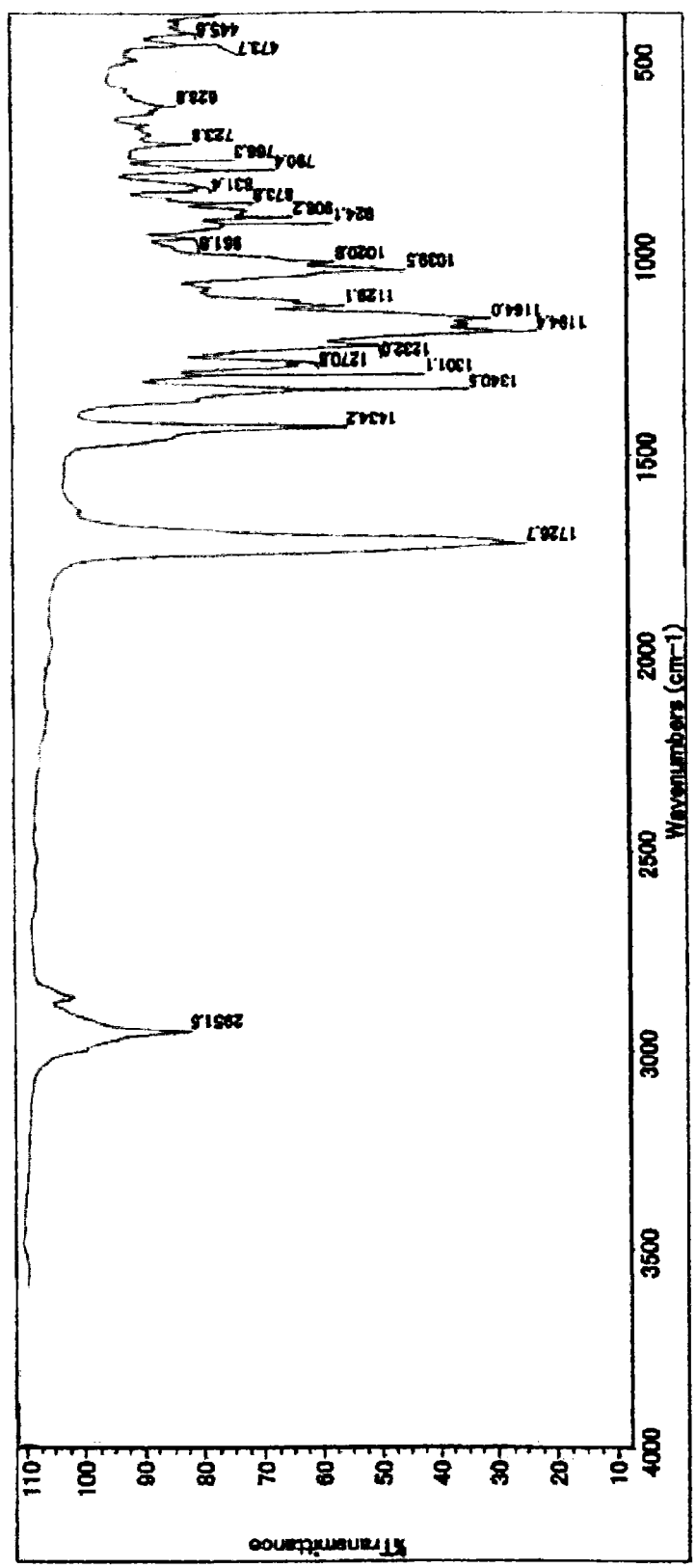
FIG. 1 is a graph showing an IR spectrum of a compound obtained in Example 1.

Hereinafter, the present invention will be described in detail based on preferred embodiments thereof.

First, a method for producing an ester compound of the present invention is described. The method for producing an ester compound of the present invention is a method for producing an ester compound, comprising reacting a compound having at least one cyclic structure of a norbornene ring and a norbornadiene ring with an alcohol and carbon monoxide by using a palladium catalyst and an oxidizing agent, to thereby introduce ester groups to carbon atoms forming a double bond in the cyclic structure and obtain the ester compound, wherein the palladium catalyst comprises a palladium acetate having a nitrite ligand in an amount of 10% by mole or more in terms of metal, and the palladium acetate having a nitrite ligand is represented by the following general formula (1):

$$Pd_3(CH_3COO)_5(NO_2) \qquad (1)$$

(hereinafter, this palladium acetate having a nitrite ligand and being represented by general formula (1) is abbreviated as "Pd$_3$(OAc)$_5$(NO$_2$)" in some cases).

The palladium catalyst according to the present invention is a palladium catalyst comprising the palladium acetate having a nitrite ligand (Pd$_3$(OAc)$_5$ (NO$_2$)) in an amount of 10% by mole or more in terms of metal. If the content ratio of the palladium acetate having a nitrite ligand in the palladium catalyst is less than the lower limit, it is difficult to sufficiently suppress the formation of by-products, so that it is difficult to produce the ester compound with a sufficiently high selectivity. In addition, in the palladium catalyst, the content ratio of the palladium acetate having a nitrite ligand (Pd$_3$(OAc)$_5$ (NO$_2$)) is preferably 30% by mole or more, more preferably 40% by mole or more, further preferably 50% by mole or more, and particularly preferably 70% by mole to 100% by mole in terms of metal (relative to the total amount of palladium in the palladium catalyst), from the viewpoint that the formation of by-products can be suppressed at a higher level, and the ester compound can be produced with a higher selectivity.

In addition, components (other catalyst components) which are other than the palladium acetate having a nitrite ligand and which may be contained in the palladium catalyst are not particularly limited, and it is possible to use, as appropriate, known palladium-based catalyst components which can be used for alkoxycarbonylation (esterification) of a carbon-carbon double bond (olefinic double bond) in a norbornene ring and a norbornadiene ring (such as palladium chloride, palladium nitrate, palladium sulfate, palladium acetate, palladium propionate, palladium carbon, palladium alumina, and palladium black). In addition, from the viewpoints of the suppression of polymerization products and by-products and improvement in selectivity, it is preferable to use palladium acetate as a component (palladium-based catalyst component) which is other than the palladium acetate having a nitrite ligand and which may be contained in the palladium catalyst. As described above, it is possible to suitably use, as the palladium catalyst, a mixture catalyst of the palladium acetate having a nitrite ligand (Pd$_3$(OAc)$_5$(NO$_2$)) and palladium acetate in which the content ratio of the palladium acetate having a nitrite ligand is 10% by mole or more or a catalyst consisting of the palladium acetate having a nitrite ligand (Pd$_3$(OAc)$_5$(NO$_2$)).

Meanwhile, a method for producing the palladium acetate having a nitrite ligand (Pd$_3$(OAc)$_5$(NO$_2$)) is not particularly limited, and a known method can be employed, as appropriate. For example, the method described in pages 1989 to 1992 of Dalton Trans (vol. 11) published on Jun. 7, 2005 (authors: Vladimir I, Bakhmutov, et al.) or the like may be employed, as appropriate. Specifically, as the method for producing the palladium acetate having a nitrite ligand (Pd$_3$(OAc)$_5$(NO$_2$)), for example, it is possible to employ a production method in which palladium metal is dispersed in acetic acid; then nitric acid is added dropwise thereto; the reaction is allowed to proceed by heating and stirring the obtained mixture liquid under reflux with stirring; and then purple columnar crystals (crystals of the compound represented by the formula: Pd$_3$(OAc)$_5$(NO$_2$)) are taken out from the obtained solid contents. When this method for producing the palladium acetate having a nitrite ligand (Pd$_3$(OAc)$_5$(NO$_2$)) is employed, the temperature condition for heating and stirring the mixture liquid is preferably 60 to 150° C. In addition, after the mixture liquid is heated and stirred, the mixture liquid is preferably concentrated under a slow and mild condition (for example, such a condition that the pressure is reduced at once to a pressure of about 100 to 500 hPa under a temperature condition of 20 to 80° C. by using an evaporator, and then the pressure is further reduced from the reduced pressure state (about 100 to 500 hPa) to about 1 to 5 hPa over 10 to 30 minutes), from the viewpoint that crystals are grown in the mixture liquid. Then, after the mixture liquid is concentrated as described above, the mixture liquid is cooled to about room temperature, so that the crystals can be precipitated. Note that since the thus precipitated crystals may contain crystals of compounds other than crystals of Pd$_3$(OAc)$_5$(NO$_2$), the crystals (purple columnar crystals) of Pd$_3$(OAc)$_5$(NO$_2$) are selected and taken out from the precipitated crystals by employing a known method, as appropriate, in order to obtain the palladium acetate having a nitrite ligand (Pd$_3$(OAc)$_5$(NO$_2$)). Note that when such a production method is employed, a purification step of removing impurities or the like may be conducted, as appropriate, after the crystals are obtained. In addition, as the palladium catalyst according to the present invention, the palladium acetate having a nitrite ligand (Pd$_3$(OAc)$_5$(NO$_2$)) obtained as described above may be used as it is, or in the form of a mixture after being mixed, as appropriate, with other components within the above-described mole ratio range. Note that the structure of the palladium acetate having a nitrite ligand (Pd$_3$(OAc)$_5$(NO$_2$)) can be verified by NMR measurement or the like.

Moreover, the oxidizing agent according to the present invention is not particularly limited, as long as the oxidizing agent is a compound capable of oxidizing $Pd^0$ to $Pd^{2+}$, when $Pd^{2+}$ in the palladium catalyst is reduced to $Pd^0$ during the reaction (oxidative alkoxycarbonylation (esterification) reaction) for introducing the ester groups (a compound capable of reoxidizing the reduced palladium catalyst). Examples of the oxidizing agent include copper compounds such as copper chloride, copper acetate, $Cu(acac)_2$, copper benzoate, copper carbonate, and copper nitrate; iron compounds such as iron chloride, iron acetate, iron sulfate, and iron nitrate; manganese compounds such as manganese chloride, manganese acetate, and manganese oxide; zinc compounds such as zinc chloride and zinc acetate; vanadium compounds such as vanadium chloride; chlorides such as chromium chloride, tin chloride, bismuth chloride, mercury chloride, and phosphorus chloride; heteropoly acids such as molybdovanadophosphoric acid; hydrogen peroxide; and the like. More specific examples of the oxidizing agent include copper(II) chloride, copper(II) nitrate, copper(II) sulfate, copper(II) acetate, iron (III) chloride, iron(III) nitrate, iron(III) sulfate, iron(III) acetate, manganese dioxide, manganese acetate, and the like. Note that, it is also possible to oxidize $Pd^0$ to $Pd^{2+}$ by using a gas component such as oxygen or air with an oxidizing agent such as a metal or a metal compound, or the like (the above-described copper compound or the like). In addition, the oxidizing agent is preferably a copper compound, and particularly preferably copper chloride, from the viewpoint that $Pd^0$ can be efficiently oxidized to $Pd^{2+}$.

In addition, in the present invention, the compound having at least one cyclic structure of a norbornene ring and a norbornadiene ring is a raw material compound used for obtaining the ester compound by introducing ester groups to the carbon-carbon double bond (olefinic double bond) in the cyclic structure (hereinafter, the compound having at least one cyclic structure of a norbornene ring and a norbornadiene ring is simply referred to as "raw material compound," in some cases). The raw material compound will be described more specifically. This compound only needs to have, in its structure, at least one of a cyclic structure comprising a norbornene ring represented by the following structural formula (2):

[Chem. 1]

(2)

and a cyclic structure comprising a norbornadiene ring represented by the following structural formula (3):

[Chem. 2]

(3)

The other parts in the structure of the compound are not particularly limited. Specifically, the raw material compound only needs to have the cyclic structure, and examples thereof include optionally substituted norbornenes; optionally substituted norbornadienes; compounds in each of which an optionally substituted norbornene and/or norbornadiene is bound to another organic compound (for example, a linear hydrocarbon, a branched hydrocarbon, or an unsaturated hydrocarbon); condensed-ring compounds or Spiro compounds each formed by at least one of a norbornene ring and a norbornadiene ring with another cyclic hydrocarbon (which may have a substituent and may have a heteroatom in the ring); and the like.

As described above, the raw material compound only needs to have the cyclic structure, and the so-called norbornenes, norbornadienes, derivatives thereof, and the like can be used as appropriate. In addition, although the raw material compound is not particularly limited, at least one of compounds represented by the following general formulae (4) to (11) can be preferably used:

[Chem. 3]

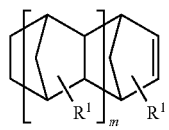
(4)

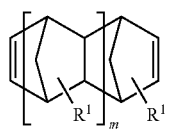
(5)

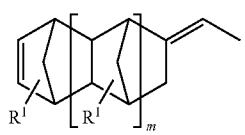
(6)

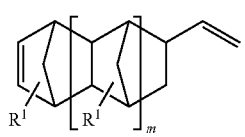
(7)

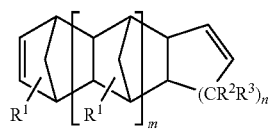
(8)

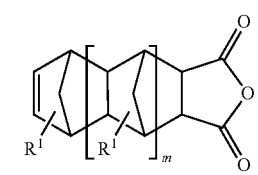
(9)

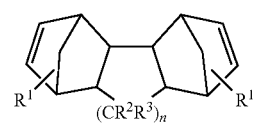
(10)

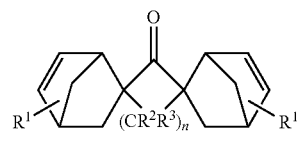
(11)

[in the formulae, R¹s, R²s, and R³s each independently represent one selected from the group consisting of a hydrogen atom, alkyl groups having 1 to 10 carbon atoms, and a fluorine atom, n represents an integer of 0 to 12, and m represents an integer of 0 to 5.

If the number of carbon atoms of the alkyl group which can be selected as each R¹ in the general formulae (4) to (11) exceeds the upper limit, the production and purification tend to be difficult. In addition, from the viewpoint of the ease of production and purification, the number of carbon atoms of the alkyl group which can be selected as R¹ is preferably 1 to 5, and more preferably 1 to 3. In addition, the alkyl group which can be selected as R¹ may be linear or branched. Moreover, R¹s in the above-described general formulae (4) to (11) are more preferably each independently a hydrogen atom or an alkyl group having 1 to 10 carbon atoms from the viewpoint of the ease of production and purification. Especially, from the viewpoints that the raw material is readily available and that the purification is easier, R¹s are more preferably each independently a hydrogen atom, a methyl group, an ethyl group, a n-propyl group, or an isopropyl group, and particularly preferably a hydrogen atom or a methyl group. In addition, the multiple R¹s in each of the formulae are particularly preferably the same, from the viewpoints of the ease of production and purification and the like.

In addition, in the general formulae (4) to (11), the alkyl groups having 1 to 10 carbon atoms which can be selected as R²s and R³s are the same as the alkyl groups having 1 to 10 carbon atoms which can be selected as R¹s. Of these substituents, the substituent which can be selected as each of R²s and R³s is preferably a hydrogen atom or an alkyl group having 1 to 10 carbon atoms (more preferably 1 to 5, and further preferably 1 to 3 carbon atoms), and particularly preferably a hydrogen atom or a methyl group, from the viewpoint of ease of purification.

In addition, n in each of the above-described general formulae (4) to (11) represents an integer of 0 to 12. If the value of n exceeds the upper limit, it is difficult to produce and purify the compound represented by each of the above-described general formulae (4) to (11). In addition, an upper limit value of the numeric value range of n in the general formulae (4) to (11) is more preferably 5, and particularly preferably 3, from the viewpoint that the production and purification are easier. Meanwhile, a lower limit value of the numeric value range of n in the general formulae (4) to (11) is more preferably 1, and particularly preferably 2, from the viewpoint of the stability of the raw material. In sum, n in the general formulae (4) to (11) is particularly preferably an integer of 2 to 3.

Moreover, m in each of the above-described general formulae (4) to (11) represents an integer of 0 to 5. If the value of m exceeds the upper limit, it is difficult to produce and purify the compound represented by each of the above-described general formulae (4) to (11). In addition, an upper limit value of the numeric value range of m in the general formulae (4) to (11) is more preferably 3, and particularly preferably 1, from the viewpoints of production and purification. Meanwhile, a lower limit value of the numeric value range of m in the general formulae (4) to (11) is particularly preferably 0, from the viewpoints of production and purification. In sum, m in the general formulae (4) to (11) is particularly preferably an integer of 0 to 1.

Moreover, more specific examples of the raw material compounds represented by the general formulae (4) to (11) include compounds represented by the following general formulae (12) to (25) and the like:

[Chem. 4]

(12)

(13)

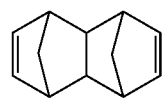

(14)

(15)

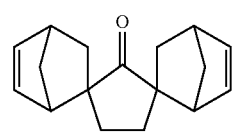

(16)

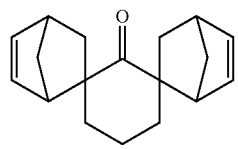

(17)

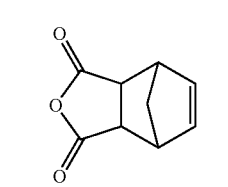

(18)

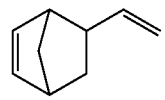

(19)

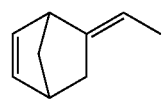

(20)

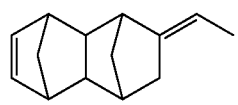

(21)

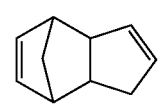

(22)

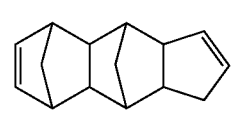

(23)

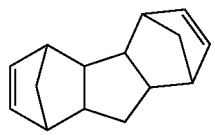
(24)

(25)

In addition, a method for preparing the raw material compound is not particularly limited, and a known method can be employed, as appropriate. For example, when a compound (spiro compound) represented by the above-described general formula (11) is used as the raw material compound, the method for preparing a spiro compound disclosed in International Publication No. WO2011/099518 may be used, as appropriate.

In addition, the alcohol according to the present invention is not particularly limited, as long as the alcohol can be used for the esterification reaction of a norbornene. Especially, from the viewpoint of the ease of production and purification, the alcohol is preferably an alcohol represented by the following general formula (26):

$$R^4OH \qquad (26)$$

[in the formula (26), $R^4$ represents one selected from the group consisting of alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms]. In other words, it is preferable to use, as the alcohol, an alkyl alcohol having 1 to 10 carbon atoms, a cycloalkyl alcohol having 3 to 10 carbon atoms, an alkenyl alcohol having 2 to 10 carbon atoms, an aryl alcohol having 6 to 20 carbon atoms, or an aralkyl alcohol having 7 to 20 carbon atoms.

The alkyl group which can be selected as $R^4$ in the general formula (26) is an alkyl group having 1 to 10 carbon atoms. If the number of carbon atoms of the alkyl group exceeds 10, it tends to be difficult to purify the obtained ester compound. In addition, the number of carbon atoms of the alkyl group which can be selected as $R^4$ is more preferably 1 to 5, and further preferably 1 to 3, from the viewpoint that the production and the purification are easier. In addition, the alkyl group which can be selected as $R^4$ may be linear or branched.

Meanwhile, the cycloalkyl group which can be selected as $R^4$ in the general formula (26) is a cycloalkyl group having 3 to 10 carbon atoms. If the number of carbon atoms of the cycloalkyl group exceeds 10, it tends to be difficult to produce and purify the obtained ester compound. In addition, the number of carbon atoms of the cycloalkyl group which can be selected as $R^4$ is more preferably 3 to 8, and further preferably 5 to 6, from the viewpoint that the production and the purification are easier.

Moreover, the alkenyl group which can be selected as $R^4$ in the above-described general formula (26) is an alkenyl group having 2 to 10 carbon atoms. If the number of carbon atoms of the alkenyl group exceeds 10, it tends to be difficult to produce and purify the obtained ester compound. In addition, the number of carbon atoms of the alkenyl group which can be selected as $R^4$ is more preferably 2 to 5, and further preferably 2 to 3, from the viewpoint that the production and the purification are easier.

Meanwhile, the aryl group which can be selected as $R^4$ in the above-described general formula (26) is an aryl group having 6 to 20 carbon atoms. If the number of carbon atoms of the aryl group exceeds 20, it tends to be difficult to produce and purify the obtained ester compound. In addition, the number of carbon atoms of the aryl group which can be selected as $R^4$ is more preferably 6 to 10, and further preferably 6 to 8, from the viewpoint that the production and the purification are easier.

Meanwhile, the aralkyl group which can be selected as $R^4$ in the above-described general formula (26) is an aralkyl group having 7 to 20 carbon atoms. If the number of carbon atoms of the aralkyl group exceeds 20, it tends to be difficult to produce and purify the obtained ester compound. In addition, the number of carbon atoms of the aralkyl group which can be selected as $R^4$ is more preferably 7 to 10, and further preferably 7 to 9, from the viewpoint that the production and the purification are easier.

Moreover, from the viewpoint that the obtained ester compound is easier to produce and purify, $R^4$ in the above-described general formula (26) is preferably each independently a hydrogen atom, a methyl group, an ethyl group, a n-propyl group, an isopropyl group, a n-butyl group, an isobutyl group, a sec-butyl group, a t-butyl group, a 2-ethylhexyl group, a cyclohexyl group, an allyl group, a phenyl group, or a benzyl group, and is particularly preferably a methyl group.

Examples of the alcohol include methanol, ethanol, butanol, allyl alcohol, cyclohexanol, benzyl alcohol, and the like. Of these alcohols, methanol and ethanol are more preferable, and methanol is particularly preferable, from the viewpoint that the obtained ester compound is easier to produce and purify. In addition, one of these alcohols may be used alone, or two or more thereof may be used as a mixture.

Meanwhile, the reaction in which the compound (raw material compound) having at least one cyclic structure of a norbornene ring and a norbornadiene ring is reacted with an alcohol and carbon monoxide to introduce ester groups to carbon atoms forming a double bond in the cyclic structure is a reaction (oxidative alkoxycarbonylation reaction: hereinafter, simply referred to as "esterification reaction" in some cases) in which the ester compound is obtained by reacting the raw material compound with the alcohol ($R^4OH$) and carbon monoxide (CO) by using a palladium catalyst and an oxidizing agent, to introduce an ester group represented by the following general formula (27):

$$—COOR^4 \qquad (27),$$

[in formula (27), $R^4$ has the same meaning as that of $R^4$ in the above-described general formula (26)] to each of the two carbon atoms forming a double bond (olefinic double bond (—C=C—)) of the cyclic structure (norbornene ring and/or norbornadiene ring) contained in the raw material compound (in each position in which the ester group is introduced, each of $R^4$s may be the same or different). Note that this esterification reaction is described by showing, in the reaction formula (I), an example of the reaction occurring at the portion of the cyclic structure in the reaction for introducing ester groups to the double bond in the cyclic structure comprising a norbornene ring (the structure represented by the above-described structural formula (2)) in the raw material compound, and, in the reaction formula (II), an example of the reaction occurring at the portion of the cyclic structure in the reaction for introducing ester groups to the double bonds of the a cyclic structure comprising a norbornadiene ring (the structure represented by the above-described structural formula (3)) in the raw material compound. These reactions for introducing ester groups to the portions of the cyclic structures are as represented by the following reaction formulae (I) and (II):

[Chem. 5]

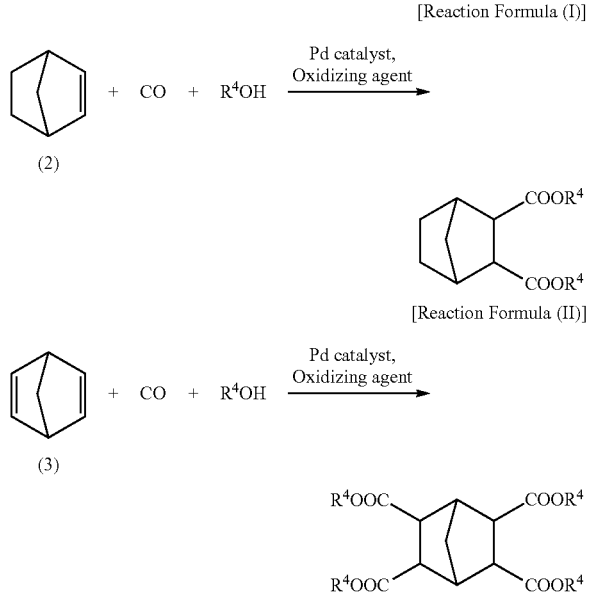

[Reaction Formula (I)]

[Reaction Formula (II)]

[in the reaction formulae (I) and (II), $R^4$s have the same meaning as that of $R^4$ in the above-described general formula (27); note that the multiple $R^4$s may be the same or different]. In the present invention, as shown in the reaction formulae (I) and (II), the esterification reaction is conducted by reacting the raw material compound having at least one cyclic structure of a norbornene ring and a norbornadiene ring with the alcohol and carbon monoxide, so that the ester group is introduced (added) to each of the carbon atoms forming a carbon-carbon double bond of the cyclic structure (norbornene ring and/or norbornadiene ring) in the raw material compound, and the ester compound (the compound in which at least the portion of the cyclic structure in the raw material compound is esterified as shown in the reaction formula (I) and/or (II)) is obtained. Moreover, such an esterification reaction is described, while a case where, for example, a spiro compound represented by the above-described general formula (11) is used as the raw material compound is taken as an example. The esterification reaction is as represented by the following reaction formula (III):

[Chem. 6]

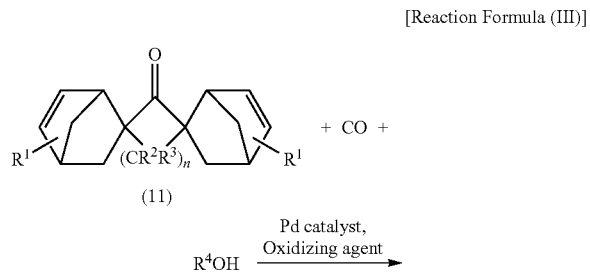

[Reaction Formula (III)]

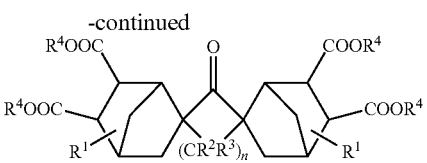

[in the reaction formula (III), $R^1$s, $R^2$s, $R^3$s, and n have the same meanings as those of $R^1$s, $R^2$s, $R^3$s, and n in the above-described general formula (11), and $R^4$s have the same meanings as those of $R^4$s in the above-described general formula (26); note that the multiple $R^4$s may be the same or different]. Note that, in the esterification reaction, when the raw material compound is a compound having a structure containing a double bond (for example, a chainlike or cyclic unsaturated hydrocarbon) other than the cyclic structure (norbornene ring and norbornadiene ring), ester groups may be introduced to the carbon atoms forming the double bond in the structure other than the cyclic structure, along with the above-described esterification reaction. Meanwhile, when the raw material compound itself has a carboxylic anhydride group (—CO—O—CO—), the carboxylic anhydride group may be reacted with the alcohol to form an ester group, along with the above-described esterification reaction.

The amount of the palladium catalyst used in the esterification reaction is preferably such that the amount of moles of palladium in the palladium catalyst (the amount of moles of the palladium catalyst in terms of Pd metal) is 0.00001 to 1 time (more preferably 0.0001 to 1 time, further preferably 0.001 to 0.1 times, and particularly preferably 0.0025 to 0.1 times) the amount of moles of the raw material compound (it is also preferable that the amount of moles of palladium be 0.01 to 0.1 times the amount of moles of the raw material compound). If the amount (amount of moles) of the palladium catalyst used is less than the lower limit, the reaction rate tends to decrease, and the percentage yield of the target product tends to decrease. Meanwhile, if the amount exceeds the upper limit, the reaction rate tends to increase, the reaction tends to proceed in a moment, and the reaction tends to be difficult to control.

Meanwhile, the amount of moles of the oxidizing agent used in the esterification reaction is preferably 2 to 16 times (more preferably 2 to 8 times, and particularly preferably 2 to 6 times) the amount of moles of the raw material compound. If the amount (amount of moles) of the oxidizing agent used is less than the lower limit, the reaction rate tends to decrease, and the percentage yield of the target product tends to decrease. Meanwhile, if the amount exceeds the upper limit, the reaction rate tends to increase, the reaction tends to proceed in a moment, and the reaction tends to be difficult to control.

Meanwhile, the amount of the alcohol used in the esterification reaction is not particularly limited, as long as the ester compound can be obtained with the amount. The amount of the alcohol used can be set, as appropriate, according to the kind of the raw material compound and the like. For example, it is possible to add the alcohol in an amount equal to or more than an amount (theoretical amount) theoretically necessary for obtaining the ester compound by the esterification of the raw material compound, and use the excessive portion of the alcohol itself as the solvent.

In addition, the amount of carbon monoxide used in the esterification reaction is not particularly limited, as long as the ester compound can be obtained with the amount. The amount of carbon monoxide used can be set, as appropriate, according to the kind of the raw material compound and the like. For example, it is possible to use carbon monoxide in an amount equal to or more than an amount (theoretical amount) theoretically necessary for obtaining the ester compound by the esterification of the raw material compound.

As described above, it is only necessary that the carbon monoxide (CO) in an amount necessary for the esterification be supplied, as appropriate, to the reaction system, in the present invention. For this reason, the gas for supplying the carbon monoxide to the reaction system may be high-purity carbon monoxide gas or a gas other than high-purity carbon monoxide gas. For example, it is possible to use carbon monoxide, a mixture gas obtained by mixing carbon monoxide with a gas inactive in the esterification reaction (for example, nitrogen or the like), or the like, and further it is also possible to use synthetic gas, coal gas, or the like. In addition, the gas for supplying carbon monoxide to the reaction system is preferably carbon monoxide or a mixture gas of carbon monoxide with another gas (nitrogen, air, oxygen, hydrogen, carbon dioxide, argon, or the like), from the viewpoint that no influence is exerted on any of the catalyst and the oxidizing agent. In addition, the carbon monoxide (CO) may be supplied to the reaction system by introducing carbon monoxide (CO) into the atmospheric gas, and the atmospheric gas may consequently form the above-described mixture gas.

In addition, it is preferable to use a solvent for the reaction (esterification reaction) of the raw material compound with the alcohol and carbon monoxide. The solvent is not particularly limited, and various solvents can be used as appropriate. It is preferable that the alcohol (for example, methanol, ethanol, propanol, or the like) used for the esterification reaction itself be used as the solvent, while being used as a raw material for the reaction. In addition, it is also possible to add another solvent to the alcohol and use in the esterification reaction. Examples of the other solvent include aromatic solvents such as benzene, toluene, xylene, and chlorobenzene; ether-based solvents such as ether, THF, and dioxane; ester-based solvents such as ethyl acetate; hydrocarbon-based solvents such as hexane, cyclohexane, heptane, and pentane; nitrile-based solvents such as acetonitrile and benzonitrile; halogen-containing solvents such as methylene chloride and chloroform; ketone-based solvents such as acetone and MEK; and amide-based solvents such as DMF, NMP, DMI, and DMAc.

In addition, the concentration of the raw material compound in the solvent is preferably 0.001 to 500 g/L, more preferably 1 to 100 g/L, and further preferably 10 to 100 g/L. If the concentration is lower than the lower limit, the reaction rate tends to decrease, and the percentage yield of the target product tends to decrease. Meanwhile, if the concentration exceeds the upper limit, the reaction rate tends to increase, the reaction tends to proceed in a moment, it tends to be difficult to control the reaction. Further, if the concentration exceeds the upper limit, the raw material or an intermediate tends to remain, and the percentage yield tends to decrease.

Moreover, since an acid is by-produced from the oxidizing agent or the like in the esterification reaction, a base may be further added to remove the acid. The base is preferably a fatty acid salt such as sodium acetate, sodium propionate, or sodium butyrate. In addition, the amount of the base used may be adjusted, as appropriate, according to the amount of the acid generated and the like.

In addition, a reaction temperature condition for the esterification reaction is not particularly limited, and is preferably 0° C. to 200° C. {more preferably 0° C. to 100° C., further preferably about 10 to 30° C., particularly preferably a temperature which is about room temperature±5° C.}. If the reaction temperature exceeds the upper limit, the yield tends to decrease. Meanwhile, if the reaction temperature is lower than the lower limit, the reaction rate tends to decrease. In addition, the reaction time of the esterification reaction is not particularly limited, and is preferably about 30 minutes to 24 hours.

In addition, the atmospheric gas in the esterification reaction is not particularly limited, and a gas usable for the esterification reaction can be used, as appropriate. For example, the atmospheric gas may be carbon monoxide or a mixture gas of carbon monoxide with another gas (nitrogen, air, oxygen, hydrogen, carbon dioxide, argon, or the like). From the viewpoint that no influence is exerted on any of the catalyst and the oxidizing agent, the atmospheric gas is preferably a mixture gas of carbon monoxide with a gas inactive in the esterification reaction (nitrogen, argon, or the like).

Moreover, a pressure condition (a pressure condition of the atmospheric gas: when the reaction is carried out in a reaction vessel, a pressure condition of the gas in the vessel) in the esterification reaction is not particularly limited, and is preferably normal pressure (0 MPaG [1 atm]) or higher and 15 MPaG or lower (normal pressure (approximately 0.1 MPa [1 atm]) or higher and 15 MPa or lower in terms of the absolute pressure), more preferably 0 MPaG or higher and 10 MPaG or lower (0.1 MPa or higher and 10 MPa or lower in terms of absolute pressure), and further preferably 0.01 MPaG or higher and 5 MPaG or lower. If the pressure condition is lower than the lower limit, the reaction rate tends to decrease, and the percentage yield of the target product tends to decrease. Meanwhile, if the pressure condition exceeds the upper limit, the reaction rate tends to increase, the reaction tends to proceed in a moment, and the reaction tends to be difficult to control.

In addition, after the esterification reaction is carried out as described above, a purification step such as recrystallization may be conducted, as appropriate, to obtain the ester compound with a higher purity. A method for the purification is not particularly limited, and a known method can be employed, as appropriate. Note that the thus obtained ester compound is a compound in which ester groups (alkoxycarbonyl groups) are introduced to at least the carbon atoms forming a double bond in the cyclic structure.

As described above, in the present invention, ester groups are introduced to the carbon atoms forming a double bond in the cyclic structure (the structure of a norbornene ring and/or a norbornadiene ring) by using the palladium catalyst (an olefinic double bond in the cyclic structure is subjected to bisalkoxycarbonylation). Thus, the formation of by-products (a polymerization product formed by addition polymerization of the portion of the cyclic structure, reaction intermediates formed because the reaction does not proceed completely, and the like) is sufficiently suppressed, so that the ester compound can be produced with a sufficiently high selectivity. In other words, according to the present invention, the ester compound can be produced with a sufficiently high selectivity. Hence, the formation of the by-products, which are difficult to separate because of emulsification upon extraction and which are difficult to separate and remove even by purification such as recrystallization, can be sufficiently suppressed. Accordingly, the decrease in percentage yield can be sufficiently suppressed. In addition, the method for producing an ester compound of the present invention makes it possible to cause the reaction to proceed with a high conversion and a high selectivity, and hence the ester compound can be produced industrially advantageously.

Next, the palladium catalyst of the present invention is described. The palladium catalyst of the present invention is a palladium catalyst used with an oxidizing agent in a method for producing an ester compound, the method comprising reacting a compound having at least one cyclic structure of a norbornene ring and a norbornadiene ring with an alcohol and carbon monoxide, to thereby introduce ester groups to carbon atoms forming a double bond in the cyclic structure and obtain the ester compound, wherein the palladium catalyst comprises a palladium acetate having a nitrite ligand in an amount of 10% by mole or more in terms of metal, and the palladium acetate having a nitrite ligand is represented by the following general formula (1):

$$Pd_3(CH_3COO)_5(NO_2) \quad (1).$$

The palladium catalyst of the present invention is the same as the palladium catalyst described above for the method for producing an ester compound of the present invention (preferred ones are also the same). Note that the compound having at least one cyclic structure of a norbornene ring and a norbornadiene ring, the alcohol, the carbon monoxide, and the oxidizing agent are also the same as those described above for the method for producing an ester compound of the present invention (the usages and the like are also the same). As described above, the palladium catalyst of the present invention is a palladium catalyst for use in the above-described method for producing an ester compound of the present invention. This palladium catalyst makes it possible to sufficiently suppress the formation of the by-products in the reaction for alkoxycarbonylation of a carbon-carbon double bond in the cyclic structure of the above-described raw material compound, so that the ester compound can be produced efficiently with a sufficiently high selectivity.

EXAMPLES

Hereinafter, the present invention will be described more specifically on the basis of Examples and Comparative Examples. However, the present invention is not limited to Examples below.

Synthesis Example 1

Preparation of $Pd_3(OAc)_5(NO_2)$ $Pd_3(OAc)_5(NO_2)$ was prepared by the method described on page 1991 of Dalton Trans (vol. 11) published in 2005. First, Pd metal (0.304 g, 2.86 mmol) was dispersed and stirred in glacial acetic acid (manufactured by Wako Pure Chemical Industries, Ltd., under the product name of "JIS Special Grade Acetic Acid", 20 ml, concentration of acetic acid: 99% by mass) to obtain a dispersion liquid. Next, an aqueous nitric acid solution (0.3 ml: conc. nitric acid) with a concentration of 60% by mass was slowly added dropwise to the thus obtained dispersion liquid with stirring to obtain a reaction liquid. Subsequently, the reaction liquid to which the conc. nitric acid had been added dropwise was heated and stirred by reflux with stirring at a reflux temperature (118° C.) for 30 minutes. Next, the reaction liquid which had been heated and stirred was cooled to room temperature (25° C.). Then, the reaction liquid was concentrated to ⅓ by using an evaporator under such a slow and mild condition that the pressure was reduced to 130 hPa at once and then reduced from 130 hPa to 5 hPa over 30 minutes, while the reaction liquid was being heated at 50° C. Thus, a liquid concentrate was obtained. Subsequently, the obtained liquid concentrate was cooled to room temperature (25° C.). By cooling as described above, an orange powder was precipitated from the liquid concentrate. Subsequently, the precipitated powder was taken out, and then the powder was dissolved in a mixture liquid of methylene chloride (10 ml) and hexane (10 ml). The obtained solution was filtered to remove insoluble matters. Next, the solution (filtrate) from which the insoluble matters had been removed was slowly concentrated by using an evaporator in such a manner that the pressure was reduced at once to 130 hPa at room temperature (25° C.) under a nitrogen stream, and then reduced from 130 hPa to 5 hPa over 30 minutes, while the solution (filtrate) was being heated at 50° C. Thus, a mixture of two types of crystals was obtained. Note that the mixture contained orange plate-like crystals and purple columnar crystals. Here, the obtained plate-like crystals and columnar crystals were both measured by $^1$H-NMR ($CDCl_3$) to identify the types of the compounds forming the crystals. It was found that the orange plate-like crystals were $Pd_3(OAc)_6$, and the purple columnar crystals were $Pd_3(OAc)_5(NO_2)$. Then, the purple columnar crystals were manually separated from the obtained mixture of the two types of crystals to obtain $Pd_3(OAc)_5(NO_2)$ (Yield: 0.26 g, Percentage yield: 41%).

Synthesis Example 2

Preparation of $Pd_3(OAc)_6$ $Pd_3(OAc)_6$ was prepared by the method described on page 1991 of Dalton Trans (vol. 11) published in 2005. First, Pd chloride (0.50 g, 2.86 mmol) was dissolved in water (50 mL) to prepare an aqueous Pd chloride solution (50 mL). Then, to the aqueous Pd chloride solution, a mixture of Na hydroxide (1.0 g, 25 mmol) and Na formate (0.80 g, 11.7 mmol) was added to obtain a reaction liquid. By adding this mixture, a solid content (powder) was formed in the reaction liquid in a moment. After that, to aggregate the powder in the reaction liquid, the reaction liquid was stirred for 30 minutes. Thus formed powder was taken out by filtration, and the obtained powder was washed with acetone, and then dried in a vacuum. After that, the obtained powder was dispersed and stirred in glacial acetic acid (manufactured by Wako Pure Chemical Industries, Ltd., under the product name of "JIS Special Grade Acetic Acid", 20 ml) to obtain a dispersion liquid. Next, to the thus obtained dispersion liquid, a 60% by mass aqueous nitric acid solution (0.3 ml: conc. nitric acid) was slowly added dropwise with stirring. Subsequently, the reaction liquid to which the conc. nitric acid had been added dropwise was heated and stirred by reflux at a reflux temperature (118° C.) for 30 minutes with nitrogen bubbling. Next, the reaction liquid which had been heated and stirred was cooled to room temperature (25° C.). Then, the reaction liquid was concentrated to ⅓ by using an evaporator under such a slow and mild condition that the pressure was reduced to 130 hPa at once and then reduced from 130 hPa to 5 hPa over 30 minutes, while the reaction liquid was being heated at 50° C. Thus, a liquid concentrate was obtained. Subsequently, the obtained liquid concentrate was cooled to room temperature (25° C.). By cooling as described above, an orange powder was obtained from the liquid concentrate. The thus obtained orange powder was subjected to $^1$H-NMR ($CDCl_3$). The obtained powder (compound) was identified as $Pd_3(OAc)_6$. Note that the yield of $Pd_3(OAc)_6$ was 0.61 g, and the percentage yield thereof was 94%.

Example 1

To a 1000 ml glass autoclave vessel (manufactured by Taiatsu Techno Corporation under the product name of "Hyper Glasstor, model TEM-V"), methanol (600 ml), $CuCl_2$ (II) (61.1 g, 454 mmol), a norbornene compound (26.0 g, 108 mmol) represented by the following general formula (16):

[Chem. 7]

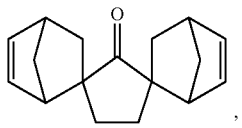

(16)

and Pd$_3$(OAc)$_5$(NO$_2$) (240 mg, 0.36 mmol) obtained in Synthesis Example 1 were introduced to obtain a mixture liquid. Then, the vessel was hermetically-sealed, and the inside atmosphere was replaced with nitrogen. Note that, the norbornene compound represented by general formula (16) was produced by employing the same method as that disclosed in Synthesis Example 1 of International Publication No. WO2011/099518. Next, while carbon monoxide was being introduced into the vessel with the pressure inside the vessel being controlled to 0.9 MPaG (partial pressure of CO was 0.9 MPa), the mixture liquid was stirred for 5 hours under conditions of 20° C. and 0.9 MPaG (partial pressure of CO: 0.9 MPa) to obtain a reaction liquid. Subsequently, carbon monoxide was removed from the inside of the vessel, and then the reaction liquid was concentrated using an evaporator. Thus, methanol was completely removed from the reaction liquid to obtain a reaction product. After that, toluene (900 ml) and 5% by mass hydrochloric acid (900 ml) were added to the reaction product, and the mixture was vigorously stirred under a temperature condition of 80° C. for 1 hour to obtain a mixture liquid. Next, the aqueous layer in the mixture liquid was discarded to obtain a toluene extraction liquid. Then, the toluene extraction liquid was again washed with 5% by mass hydrochloric acid (450 ml) under a temperature condition of 80° C. After that, the toluene extraction liquid which had been washed with the hydrochloric acid was washed twice with a saturated aqueous sodium hydrogen carbonate solution (450 ml) under a temperature condition of 80° C. Subsequently, the thus washed toluene extraction liquid was dehydrated and dried by azeotropic distillation with toluene. Subsequently, the dehydrated and dried toluene extraction liquid was concentrated using an evaporator to remove toluene by distillation. Thus, a product was obtained (Yield: 46.5 g, Percentage Yield: 89.1%).

Figure 2:
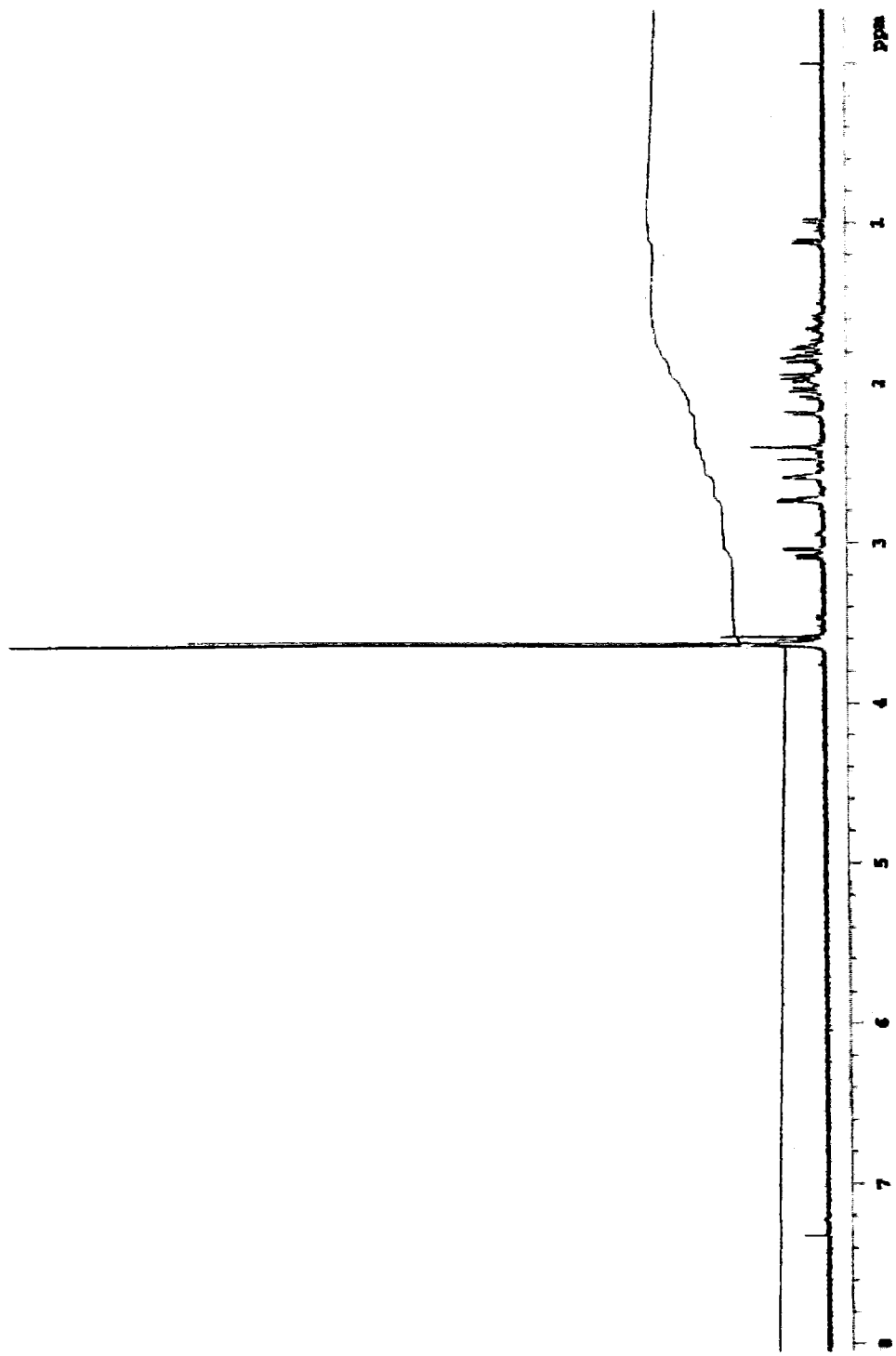
FIG. 2 is a graph showing a $^1$H-NMR (CDCl$_3$) spectrum of the compound obtained in Example 1.
Figure 3:
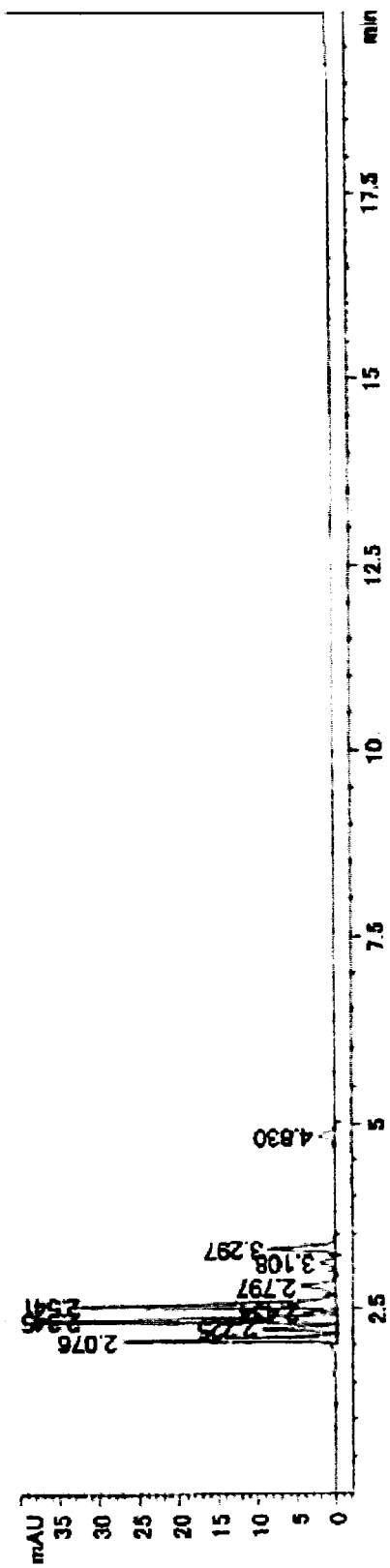
FIG. 3 is a graph showing a spectrum obtained by HPLC measurement of the compound obtained in Example 1.
Figure 4:
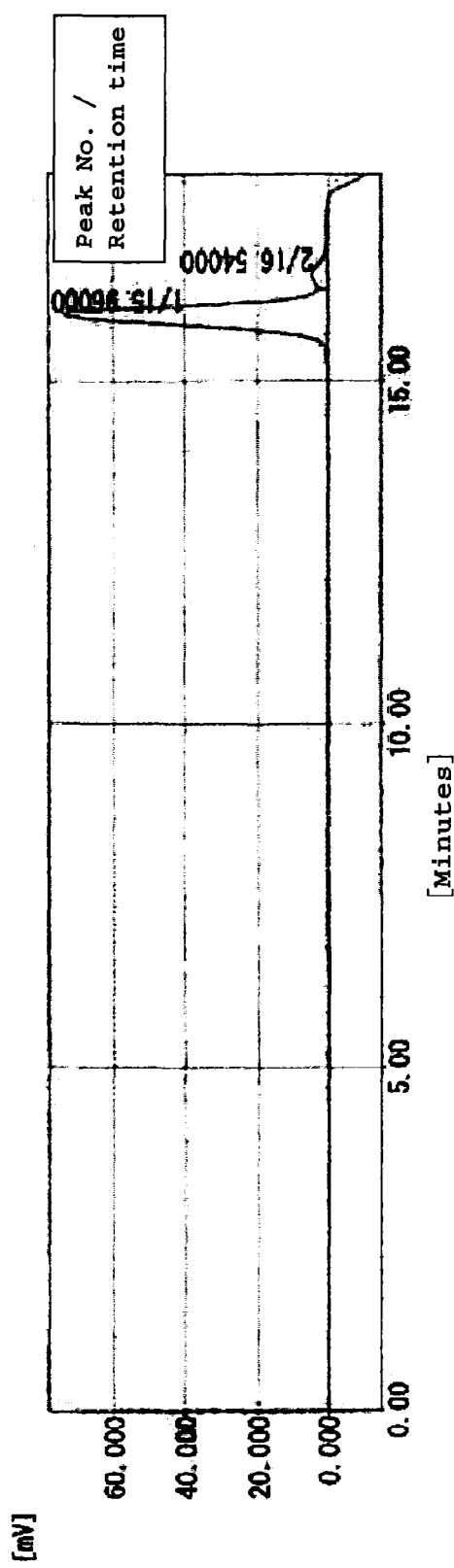
FIG. 4 is a graph showing a spectrum obtained by GPC measurement of the compound obtained in Example 1.

To determine the structure of the compound contained in the thus obtained product, IR, NMR, HPLC, and GPC measurements were conducted. As the results of these measurements, FIG. 1 shows an IR spectrum, FIG. 2 shows a $^1$H-NMR (CDCl$_3$) spectrum, FIG. 3 shows a spectrum of the HPLC measurement, and FIG. 4 shows a spectrum of the GPC measurement. As is apparent from the results shown in FIGS. 1 to 4, the compound obtained in Example 1 was identified as a norbornane tetracarboxylic acid tetramethyl ester (target compound) represented by the following general formula (28):

[Chem. 8]

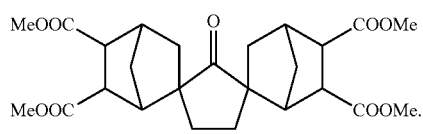

(28)

In addition, from the results of the HPLC measurement and the GPC measurement, it was found that several by-products were present in the obtained product, in addition to the above-described compound. Note that the content ratio of a reaction intermediate (hereinafter, simply referred to as "intermediate") in the obtained product was found to be 0.4% by mole from the area ratio of the HPLC spectrum, and the content ratio of a mixture (hereinafter, simply referred to as "polymerization products") of a polymerization product produced by addition polymerization of the norbornene ring in the above-described norbornene compound represented by general formula (16) and a polymerization product in which multiple norbornene rings were bound through keto groups was found to be 0.7% by mole from the results of the GPC measurement. Note that, in the spectrum shown in FIG. 3, the peaks at the positions from 2.076 to 2.797 minutes (min) are attributable to the target compound (six isomers), the peak at the position of 3.297 minutes (min) is attributable to the solvent (toluene), and the peak at the position of 4.830 minutes (min) is attributable to the intermediate. Meanwhile, in the spectrum shown in FIG. 4, the peak at the position of 15.96 minutes is attributable to the target compound, and the peak at the position of 16.54 minutes is attributable to the solvent (toluene). Moreover, the signal in a trace amount present before 15.96 minutes in FIG. 4 is attributable to the polymerization products. From these results, the percentage yield of the norbornane tetracarboxylic acid tetramethyl ester represented by general formula (28), which was the target product, was found to be 88%, and the selectivity thereof was found to be 99%. Table 1 shows the thus obtained results.

Note that, as described above, in the method for producing an ester compound employed in Example 1, the content ratio of Pd$_3$(OAc)$_5$(NO$_2$) was 1% by mole, in terms of metal, relative to the norbornene compound, the content (concentration in methanol) of the norbornene compound was 43 g/L, the pressure during the reaction was 0.9 MPaG, the temperature condition during the reaction was 20° C., and the reaction time was 20 hours.

Comparative Example 1

The compound (the target compound: the norbornane tetracarboxylic acid tetramethyl ester represented by general formula (28)) was obtained in the same manner as in Example 1, except that Pd$_3$(OAc)$_6$ obtained in Synthesis Example 2 was used instead of Pd$_3$(OAc)$_5$(NO$_2$) obtained in Synthesis Example 1 with the same amount of moles of the metal (Pd) being contained.

Comparative Example 2

The compound (the target compound: the norbornane tetracarboxylic acid tetramethyl ester represented by general formula (28)) was obtained in the same manner as in Example 1, except that Pd(NO$_3$)$_2$ (manufactured by Aldrich) was used instead of Pd$_3$(OAc)$_5$(NO$_2$) obtained in Synthesis Example 1 with the same amount of moles of the metal (Pd) being contained.

Comparative Example 3

The compound (the target compound: the norbornane tetracarboxylic acid tetramethyl ester represented by general formula (28)) was obtained in the same manner as in Example 1, except that PdCl2 (manufactured by Aldrich) was used instead of $Pd_3(OAc)_5(NO_2)$ obtained in Synthesis Example 1 with the same amount of moles of the metal (Pd) being contained.

Comparative Example 4

The compound (the target compound: the norbornane tetracarboxylic acid tetramethyl ester represented by general formula (28)) was obtained in the same manner as in Example 1, except that palladium carbon (Pd/C: manufactured by Aldrich) was used instead of $Pd_3(OAc)_5(NO_2)$ obtained in Synthesis Example 1 with the same amount of moles of the metal (Pd) being contained.

The compounds obtained in Comparative Examples 1 to 4 were each subjected to IR, NMR, HPLC, and GPC measurements as in the case of the compound obtained in Example 1. As the result of these measurements, Table 1 shows the percentage yield and selectivity of the target compound (the norbornane tetracarboxylic acid tetramethyl ester represented by general formula (28)), and the content ratios (unit: % by mole) of the intermediate and the polymerization products in each of the obtained products. Note that, in Table 1, the target compound is referred to as "target product."

TABLE 1

| | Type of palladium catalyst | Yield of target product (%) | Content ratio of intermediate (% by mole) | Content ratio of polymerization products (% by mole) | Selectivity of target product (%) |
|---|---|---|---|---|---|
| Example 1 | $Pd_3(OAc)_5(NO_2)$ | 68 | 0.4 | 0.7 | 99 |
| Comp. Ex. 1 | $Pd_3(OAc)_5$ | 49 | 6 | 29 | 58 |
| Comp. Ex. 2 | $Pd_3(NO_3)_2$ | 46 | 7 | 36 | 52 |
| Comp. Ex. 3 | $PdCl_2$ | 36 | 7 | 44 | 41 |
| Comp. Ex. 4 | Pd/C | 28 | 8 | 52 | 32 |

As is apparent from the results shown in Table 1 and the like, it was found that, in the case (Example 1) where $Pd_3(OAc)_5(NO_2)$ was used as a Pd catalyst, the formation of the by-products such as the intermediate and the polymerization products was sufficiently suppressed, and the target ester compound was formed with a sufficiently high selectivity. In addition, it was found that the target ester compound was obtained in a sufficiently high percentage yield in the case (Example 1) where $Pd_3(OAc)_5(NO_2)$ was used as the Pd catalyst. From these results, it was found that the method for producing an ester compound of the present invention in which $Pd_3(OAc)_5(NO_2)$ was used as a Pd catalyst (Example 1) was able to cause the reaction to proceed with a high conversion and a high selectivity, and achieve a sufficiently high percentage yield of the target compound (the norbornane tetracarboxylic acid tetramethyl ester represented by general formula (28)). In contrast, in the cases (Comparative Examples 1 to 4) where the Pd catalysts other than $Pd_3(OAc)_5(NO_2)$ were used, the selectivity was about 58% at the highest, and it was not possible to sufficiently suppress the formation of the by-products.

From these results, it has been found that the use of $Pd_3(OAc)_5(NO_2)$ as a Pd catalyst used for the oxidative alkoxycarbonylation reaction (esterification reaction) makes it possible to efficiently produce the target ester compound with a sufficiently high selectivity.

Examples 2 to 5 and Comparative Examples 5 and 6

First, $Pd_3(OAc)_5(NO_2)$ obtained in Synthesis Example 1 and $Pd_3(OAc)_6$ obtained in Synthesis Example 2 were mixed with each other at each of the ratios (mole ratios in terms of metal) shown in Table 2 to prepare Pd catalysts among which the content ratio of $Pd_3(OAc)_5(NO_2)$ varied.

TABLE 2

| | Palladium catalyst | |
|---|---|---|
| | Content of $Pd_3(OAc)_5(NO_2)$ (% by mole) | Content of $Pd_3(OAc)_6$ (% by mole) |
| Example 2 | 90 | 10 |
| Example 3 | 70 | 30 |
| Example 4 | 20 | 80 |
| Example 5 | 15 | 85 |
| Comp. Ex. 5 | 5 | 95 |
| Comp. Ex. 6 | 1 | 99 |

Subsequently, the compound (the target compound: the norbornane tetracarboxylic acid tetramethyl ester represented by general formula (28)) was obtained in the same manner as in Example 1, except that each of the Pd catalysts shown in Table 2 was used instead of $Pd_3(OAc)_5(NO_2)$ obtained in Synthesis Example 1 with the same amount of moles of the metal (Pd) being contained.

The compound contained in the product obtained in each of Examples 2 to 5 and Comparative Examples 5 and 6 was subjected to IR, NMR, HPLC, and GPC measurements as in the case of the compound obtained in Example 1. As the measurement results, Table 3 shows the percentage yield and selectivity of the target compound (the norbornane tetracarboxylic acid tetramethyl ester represented by general formula (28)) and the content ratios (% by mole) of the intermediate and the polymerization products in the obtained product. Note that, for reference, Table 3 also shows the measurement results of the compound obtained in Example 1. In addition, in Table 3, the target compound is referred to as "target product."

TABLE 3

|  | Content of Pd$_3$(OAc)$_5$(NO$_2$) in palladium catalyst (% by mole) | Yield of target product (%) | Content ratio of intermediate (% by mole) | Content ratio of polymerization products (% by mole) | Selectivity of target product (%) |
|---|---|---|---|---|---|
| Example 1 | 100 | 88 | 0.4 | 0.7 | 99 |
| Example 2 | 90 | 83 | 0.4 | 0.8 | 99 |
| Example 3 | 70 | 88 | 0.7 | 1 | 98 |
| Example 4 | 20 | 76 | 2 | 4 | 93 |
| Example 5 | 15 | 82 | 2 | 5 | 92 |
| Comp. Ex. 5 | 5 | 61 | 5 | 25 | 67 |
| Comp. Ex. 6 | 1 | 43 | 7 | 37 | 49 |

As is apparent from the results shown in Table 3, it was found that, in each of the cases (Examples 1 to 5) where the Pd catalysts having content ratios of Pd$_3$(OAc)$_5$(NO$_2$) of 10% by mole or more were used, the formation of the by-products such as the intermediate and the polymerization products was sufficiently suppressed, and the target ester compound was formed with a sufficiently high selectivity of 90% or higher. In addition, it was found that the target ester compound was obtained in a sufficiently high percentage yield in each of the cases (Examples 1 to 5) where the Pd catalysts having content ratios of Pd$_3$(OAc)$_5$(NO$_2$) of 10% by mole or more. From these results, it was fund that the method for producing an ester compound of the present invention (each of Examples 1 to 5) in which the catalysts having content ratios of Pd$_3$(OAc)$_5$ (NO$_2$) of 10% by mole or more were used as the Pd catalyst was able to cause the reaction to proceed with a high conversion and a high selectivity, and achieve a sufficiently high percentage yield of the target compound (the norbornane tetracarboxylic acid tetramethyl ester represented by general formula (28)). On the other hand, from the results shown in Table 1 and Table 3, it was found that, in each of the cases (Comparative Examples 1 to 6) where the Pd catalysts having content ratios of Pd$_3$(OAc)$_5$(NO$_2$) of less than 10% by mole, it was not possible to sufficiently suppress the formation of the by-products (especially, the formation of the polymerization products), the selectivity was about 67% at the highest, and it was not possible to form the target product with a sufficiently high selectivity (for example, with a selectivity of about 90% or higher).

From these results, it was found that the method for producing an ester compound of the present invention (each of Examples 1 to 5) was able to sufficiently reduce the formation of by-products, and produce the ester compound, which was the target compound, with a sufficiently high selectivity (for example, a selectivity of about 900 or higher). Especially in the cases (Examples 1 to 3) where the Pd catalysts having content ratios of Pd$_3$(OAc)$_5$(NO$_2$) of 70% by mole or more were used, it was found that each of the content ratio of the intermediate and the content ratio of the polymerization products was able to be turned into 1% by mole or less, and the target compound was able to be produced with an extremely high selectivity.

Example 6

To a 1000 ml glass autoclave vessel (manufactured by Taiatsu Techno Corporation, Hyper Glasstor, model TEM-V), methanol (600 ml), CuCl$_2$(II) (83.4 g, 620 mmol), 5-norbornene-2,3-dicarboxylic anhydride (49.5 g, 300 mmol) represented by the following general formula (18):

[Chem. 9]

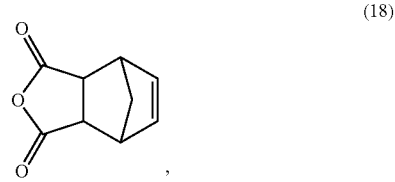

(18)

and Pd$_3$(OAc)$_5$(NO$_2$) (333 mg, 0.5 mmol) prepared in Synthesis Example 1 were introduced to obtain a mixture liquid. Then, the vessel was hermetically-sealed, and the inside atmosphere was replaced with nitrogen. Next, while carbon monoxide was introduced into the vessel with the pressure inside the vessel being controlled to 0.9 MPaG (partial pressure of CO: 0.9 MPa), the mixture liquid was stirred for 5 hours under conditions of 20° C. and 0.9 MPaG (partial pressure of CO: 0.9 MPa) to obtain a reaction liquid. Subsequently, carbon monoxide was removed from the inside of the vessel, and then the reaction liquid was concentrated using an evaporator to completely remove methanol from the reaction liquid. Thus, a reaction product was obtained. After that, chloroform (900 ml) and 5% by mass hydrochloric acid (900 ml) were added to the reaction product, and the mixture was vigorously stirred under a temperature condition of 60° C. for 1 hour to obtain a mixture liquid. Next, the aqueous layer in the mixture liquid was discarded to obtain a chloroform extraction liquid. Then, the chloroform extraction liquid was again washed with 5% by mass hydrochloric acid (450 ml) under a temperature condition of 60° C. After that, the chloroform extraction liquid which had been washed with the hydrochloric acid was washed twice with a saturated aqueous sodium hydrogen carbonate solution (450 ml) under a temperature condition of 60° C. Subsequently, the thus washed chloroform extraction liquid was dehydrated and dried over anhydrous magnesium sulfate (50 g). Subsequently, the anhydrous magnesium sulfate was filtered off, and the dehydrated and dried chloroform extraction liquid was concentrated using an evaporator to remove chloroform by distillation. Thus, a product was obtained (Yield: 94.2 g, Percentage Yield: 95.6%).

Figure 5:
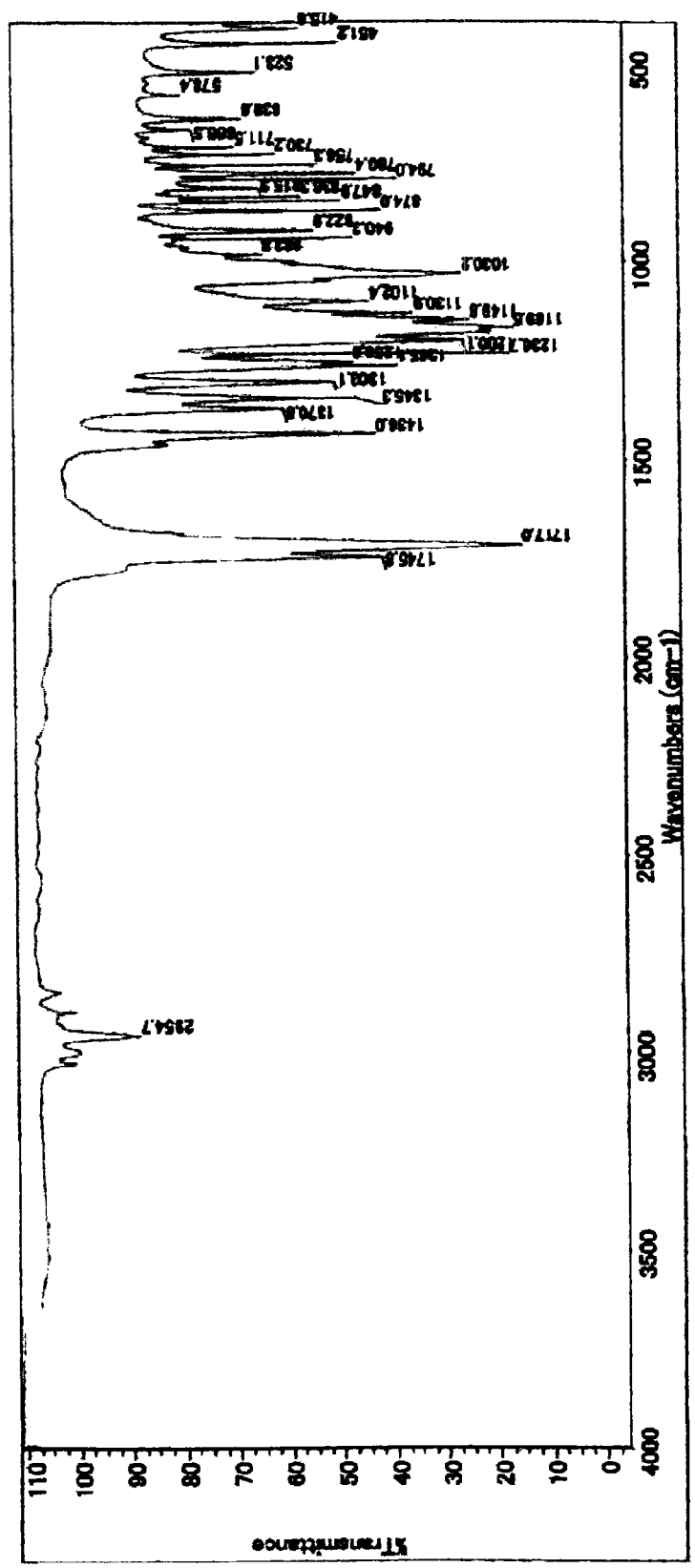
FIG. 5 is a graph showing an IR spectrum of a compound obtained in Example 6.
Figure 6:
FIG. 6 is a graph showing a $^1$H-NMR (CDCl$_3$) spectrum of a compound obtained in Example 6.
Figure 7:
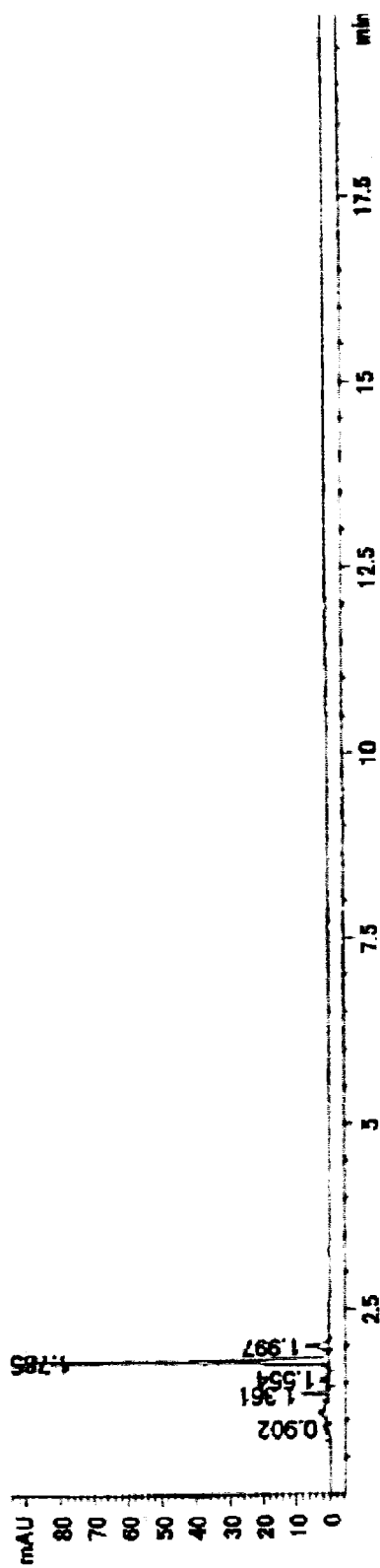
FIG. 7 is a graph showing a spectrum obtained by HPLC measurement of the compound obtained in Example 6.
Figure 8:
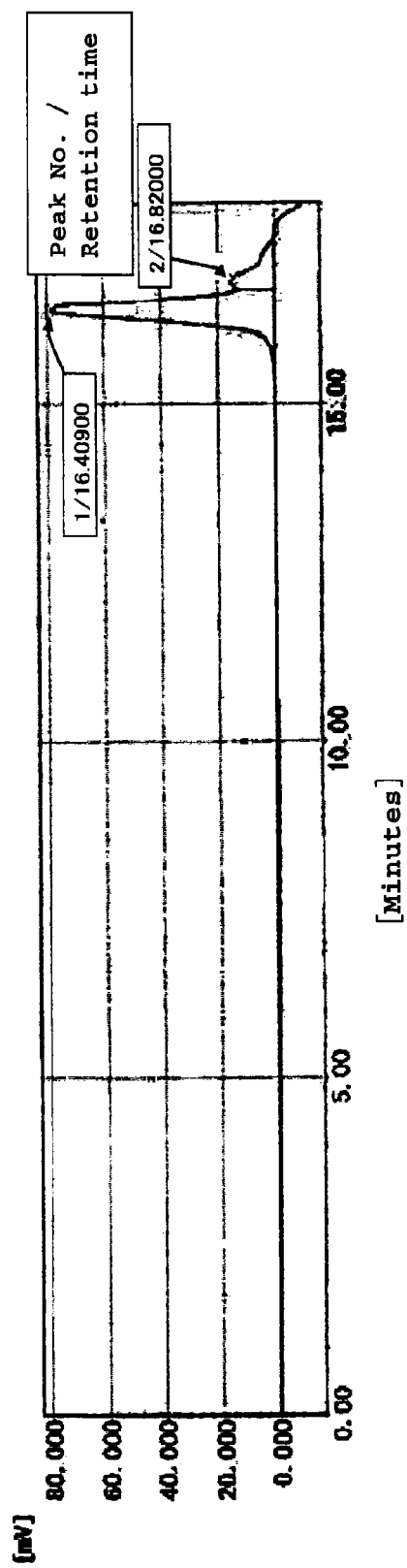
FIG. 8 is a graph showing a spectrum obtained by GPC measurement of the compound obtained in Example 6.

To determine the structure of the compound contained in the thus obtained product, IR, NMR, HPLC, and GPC measurements were conducted. As the results of these measurements, FIG. 5 shows an IR spectrum, FIG. 6 shows a $^1$H-NMR (CDCl$_3$) spectrum, FIG. 7 shows a spectrum of the HPLC measurement, and FIG. 8 shows a spectrum of the GPC measurement. As is apparent from the results shown in FIGS. 5 to 8, the compound obtained in Example 6 was identified as norbornane tetracarboxylic acid tetramethyl ester (target compound) represented by the following general formula (29):

[Chem. 10]

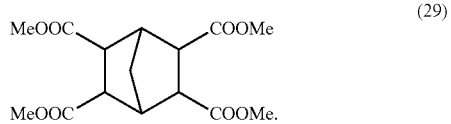

(29)

In addition, from the results of the HPLC measurement and the GPC measurement, it was found that by-products were present in the obtained product. Note that the content ratio of the reaction intermediate (hereinafter, simply referred to as "intermediate") in the obtained product was found to be 0% by mole from the area ratio of the HPLC spectrum, and the content ratio of the polymerization product formed by addition polymerization of the norbornene ring in the norbornene compound represented by the above-described general formula (18) was found to be 0.1% by mole from the results of the GPC measurement. Note that, in FIG. 7, the peaks at the positions of 1.785 and 1.997 minutes (min) are attributable to the target compound (two isomers), and the peak at the position of 1.361 minutes (min) is attributable to the solvent (chloroform). In addition, in FIG. 8, the peak at the position of 16.41 minutes is attributable to the target compound, the peak at the position of 16.82 minutes is attributable to the solvent (chloroform), and the signal in a trace amount present before 16.41 minutes is attributable to the polymerization product. From these results, it was found that the percentage yield of the norbornane tetracarboxylic acid tetramethyl ester represented by general formula (29), which was the target product, was 95.5%, and the selectivity thereof was 99%.

As is apparent from these results, it was found that, in the case (Example 6) where $Pd_3(OAc)_5(NO_2)$ was used as the Pd catalyst, the formation of the by-products such as the intermediate and the polymerization products was sufficiently suppressed, and the target ester compound was formed with a sufficiently high selectivity. In addition, it was found that the target ester compound was obtained in a sufficiently high percentage yield in the case (Example 6) where $Pd_3(OAc)_5(NO_2)$ was used as the Pd catalyst. From these results, it was found that the method for producing an ester compound of the present invention (Example 6) in which the catalyst with a content ratio of $Pd_3(OAc)_5(NO_2)$ of 10% by mole or more was used as the Pd catalyst was able to cause the reaction to proceed with a high conversion and a high selectivity, and achieve a sufficiently high percentage yield of the target compound (the norbornane tetracarboxylic acid tetramethyl ester represented by general formula (29)).

Examples 7 to 9

The compound (the target compound: the norbornane tetracarboxylic acid tetramethyl ester represented by general formula (28)) was obtained in the same manner as in Example 1, except that the amount of the palladium catalyst used was changed, so that each ratio of the amount of moles of the palladium catalyst ($Pd_3(OAc)_5(NO_2)$) obtained in Synthesis Example 1) to the amount of moles of the above-described norbornene compound represented by general formula (16) was a ratio (the ratio determined by calculation of the formula: [the ratio (%) of the amount of moles of the palladium catalyst to the amount of moles of the norbornene compound]={[$Pd_3(OAc)_5(NO_2)$]/[the norbornene compound shown in the above-described general formula (16)]}× 100) as shown in Table 4 (Note that, in each of the examples, $Pd_3(OAc)_5(NO_2)$ obtained in Synthesis Example 1 was used as the Pd catalyst as in the case of Example 1.).

The compound contained in each of the products obtained in Examples 7 to 9 were subjected to IR, NMR, HPLC, and GPC measurements as in the case of the compound obtained in Example 1. As the measurement results, Table 4 shows the percentage yield and the selectivity of the target compound (the norbornane tetracarboxylic acid tetramethyl ester represented by general formula (28)), and the content ratios (% by mole) of the intermediate and the polymerization products in the obtained product. Note that, for reference, Table 4 also shows the measurement results of the compound obtained in Example 1. In addition, in Table 4, the target compound is referred to as "target product."

TABLE 4

| | Ratio of amount of moles of palladium catalyst relative to amount of moles of norbornene compound (%) | Yield of target product (%) | Content ratio of intermediate (% by mole) | Content ratio of polymerization products (% by mole) | Selectivity of target product (%) |
|---|---|---|---|---|---|
| Example 1 | 0.33 | 88 | 0.4 | 0.7 | 99 |
| Example 7 | 0.50 | 94 | 0.9 | 1.1 | 98 |
| Example 8 | 1.0 | 94 | 0.6 | 1.0 | 98 |
| Example 9 | 0.25 | 87 | 2.2 | 2.2 | 95 |

Example 10

The compound (the target compound: the norbornane tetracarboxylic acid tetramethyl ester represented by general formula (28)) was obtained in the same manner as in Example 1, except that the amount of the above-described norbornene compound represented by general formula (16) used was changed, so that the concentration (concentration in methanol: g/L) of the norbornene compound represented by general formula (16) was equal to the ratio shown in Table 5 (note that, as the Pd catalyst, $Pd_3(OAc)_5(NO_2)$ obtained in Synthesis Example 1 was used as in the case of Example 1).

The compound contained in the product obtained in Example 10 was subjected to IR, NMR, HPLC, and GPC measurements as in the case of the compound obtained in Example 1. As the measurement results, Table 5 shows the percentage yield and the selectivity of the target compound (the norbornane tetracarboxylic acid tetramethyl ester represented by general formula (28)) and the content ratios (% by mole) of the intermediate and the polymerization products in the obtained product. Note that, for reference, Table 5 also shows the measurement results of the compound obtained in Example 1. In addition, in Table 5, the target compound is referred to as "target product."

TABLE 5

| | Concentration of norbornene compound serving as raw material compound (g/L) | Yield of target product (%) | Content ratio of intermediate (% by mole) | Content ratio of polymerization products (% by mole) | Selectivity of target product (%) |
|---|---|---|---|---|---|
| Example 1 | 43.3 | 88 | 0.4 | 0.7 | 99 |
| Example 10 | 60.0 | 90 | 1.0 | 1.3 | 98 |

Example 11

To a 1000 ml glass autoclave vessel (manufactured by Taiatsu Techno Corporation under the product name of "Hyper Glasstor, model TEM-V"), methanol (600 ml), $CuCl_2$ (II) (61.1 g, 454 mmol), the above-described norbornene compound (26.0 g, 108 mmol: the same norbornene compound as that used in Example 1) represented by general formula (16), and $Pd_3(OAc)_5(NO_2)$ (240 mg, 0.36 mmol) obtained in Synthesis Example 1 were introduced to obtain a mixture liquid. Then, the vessel was hermetically-sealed, and the inside atmosphere was replaced with nitrogen. Next, the pressure inside the vessel was reduced to a vacuum. Then, while carbon monoxide was being introduce to the vessel with the pressure inside the vessel being controlled to 0.03 MPaG (CO: 0.13 MPa: the gas in the vessel was only CO), the mixture liquid was stirred for 5 hours under conditions of 20° C. and a CO pressure of 0.13 MPa to obtain a reaction liquid. Subsequently, carbon monoxide was removed from the inside of the vessel, and then the reaction liquid was concentrated using an evaporator to completely remove methanol from the reaction liquid. Thus, a reaction product was obtained. After that, toluene (900 ml) and 5% by mass hydrochloric acid (900 ml) were added to the reaction product, and the mixture was vigorously stirred under a temperature condition of 80° C. for 1 hour. Thus, a mixture liquid was obtained. Next, the aqueous layer in the mixture liquid was discarded to obtain a toluene extraction liquid. Then, the toluene extraction liquid was again washed with 5% by mass hydrochloric acid (450 ml) under a temperature condition of 80° C. After that, the toluene extraction liquid which had been washed with the hydrochloric acid was washed twice with a saturated aqueous sodium hydrogen carbonate solution (450 ml) under a temperature condition of 80° C. Subsequently, the thus washed toluene extraction liquid was dehydrated and dried by azeotropic distillation with toluene. Subsequently, the dehydrated and dried toluene extraction liquid was concentrated using an evaporator to remove toluene by distillation. Thus, a product was obtained.

The compound contained in the product obtained in Example 11 was subjected to IR, NMR, HPLC, and GPC measurements as in the case of the compound obtained in Example 1. From the results of these measurements, the compound obtained in Example 11 was identified as the norbornane tetracarboxylic acid tetramethyl ester (target compound: the same as the target compound in the Example 1) represented by the above-described general formula (28). Moreover, as the measurement results, Table 6 shows the percentage yield and the selectivity of the target compound (the above-described norbornane tetracarboxylic acid tetramethyl ester represented by general formula (28)), and the content ratios (% by mole) of the intermediate and the polymerization products in the obtained product. Note that, for reference, Table 6 also shows the measurement results of the compound obtained in Example 1. In addition, in Table 6, the target compound is referred to as "target product."

TABLE 6

| | CO pressure in vessel (MPa) | Yield of target product (%) | Content ratio of intermediate (% by mole) | Content ratio of polymerization products (% by mole) | Selectivity of target product (%) |
|---|---|---|---|---|---|
| Example 1 | 0.9 | 88 | 0.4 | 0.7 | 99 |
| Example 11 | 0.13 | 87 | 0.8 | 1.8 | 97 |

As is apparent from the results shown in Tables 4 to 6, it was found that, in each of the cases (Examples 7 to 11) where $Pd_3(OAc)_5(NO_2)$ was used as the Pd catalyst in the method for producing an ester compound, the formation of the by-products such as the intermediate and the polymerization products was sufficiently suppressed, and the target ester compound was formed with a sufficiently high selectivity. In addition, as shown in Tables 4 to 6, it was found that the target ester compound was obtained in a sufficiently high percentage yield in each of the cases (Examples 7 to 11) where $Pd_3(OAc)_5(NO_2)$ was used as the Pd catalyst. From these results, it was found that the method for producing an ester compound of the present invention (each of Examples 7 to 11) in which $Pd_3(OAc)_5(NO_2)$ was used as the Pd catalyst was able to cause the reaction to proceed with a high conversion and a high selectivity, and achieve a sufficiently high percentage yield of the target compound (the norbornane tetracarboxylic acid tetramethyl ester represented by general formula (28)).

From the above-described results, it was found that the method for producing an ester compound of the present invention (each of Examples 1 to 11) in which a catalyst having a content ratio of $Pd_3(OAc)_5$ $(NO_2)$ of 10% by mole or more was used as the Pd catalyst and in which a compound having a cyclic structure comprising a norbornene ring in its structure was used as a raw material compound was able to efficiently introduce (add) ester groups to the carbon atoms forming the double bond of the norbornene ring in the compound and form the target ester compound with a sufficiently high selectivity.

INDUSTRIAL APPLICABILITY

As described above, according to the present invention, it is possible to provide a method for producing an ester compound by which the formation of by-products can be sufficiently suppressed, and the ester compound can be produced efficiently with a sufficiently high selectivity, as well as a palladium catalyst used in the method.

Accordingly, since the method for producing an ester compound of the present invention makes it possible to produce an ester compound with a sufficiently high selectivity, this method is especially useful as a method for industrially producing an ester compound which can be used for various applications (for example, as a monomer of polyimide and the like), and the like.

The invention claimed is:

1. A method for producing an ester compound comprising reacting a compound having at least one cyclic structure of a norbornene ring and a norbornadiene ring with an alcohol and carbon monoxide in the presence of a palladium-containing catalyst composition adapted for producing the ester compound and an oxidizing agent, to thereby introduce ester groups to carbon atoms forming a double bond in the cyclic structure and obtain the ester compound, wherein said palladium-containing catalyst composition comprises a palladium acetate having a nitrite ligand in an amount of 10% by mole or more in terms of metal, and the palladium acetate having a nitrite ligand is represented by the following general formula (1):

$$Pd_3(CH_3COO)_5(NO_2) \qquad (1); \text{ and,}$$

wherein said oxidizing agent is capable of oxidizing $Pd^0$ to $Pd^{2+}$.

2. The method for producing an ester compound according to claim 1, wherein the palladium catalyst comprises the palladium acetate having a nitrite ligand in an amount of 30% by mole or more in terms of metal.

3. A palladium-containing catalyst composition adapted for use with an oxidizing agent for producing an ester compound obtained by a method comprising reacting a compound having at least one cyclic structure of a norbornene ring and a norbornadiene ring with an alcohol and carbon monoxide in the presence of said palladium-containing catalyst composition and said oxidizing agent, to thereby introduce ester groups to carbon atoms forming a double bond in the cyclic structure and obtain said ester compound, wherein said palladium-containing catalyst composition comprises a palladium acetate having a nitrite ligand in an amount of 10% by mole or more in terms of metal, and the palladium acetate having a nitrite ligand is represented by the following general formula (1):

$$Pd_3(CH_3COO)_5(NO_2) \qquad (1); \text{ and}$$

wherein said oxidizing agent is capable of oxidizing $Pd^0$ to $Pd^{2+}$.

4. The palladium catalyst according to claim 3, wherein the palladium catalyst comprises the palladium acetate having a nitrite ligand in an amount of 30% by mole or more in terms of metal.

* * * * *